United States Patent [19]

Nimni

[11] Patent Number: 4,820,724
[45] Date of Patent: Apr. 11, 1989

[54] DUAL PHASE SOLVENT CARRIER SYSTEM

[75] Inventor: Marcel E. Nimni, Santa Monica, Calif.

[73] Assignee: University of Southern California, Los Angeles, Calif.

[21] Appl. No.: 846,171

[22] Filed: Mar. 31, 1986

[51] Int. Cl.⁴ .................. A61K 31/415; A61K 31/34; A61K 31/21; A61K 31/12

[52] U.S. Cl. ..................................... 514/396; 514/397; 514/399; 514/462; 514/514; 514/675; 514/724; 514/730; 514/858; 514/947

[58] Field of Search .............. 514/399, 396, 397, 462, 514/514, 675, 724, 730, 858, 947

[56] References Cited

U.S. PATENT DOCUMENTS 3,899,578  8/1975  Bird et al. ........................... 424/81

OTHER PUBLICATIONS

Handbook of Nonprescription Drugs 6th ed. p. 449, Product NP27 liquid, 1980.
ASMC, Dermato-Venereologica, pp. 454–460 (1959).
British Journal of Dermatology, vol. 91, pp. 49–55 (1974).
Journal Internationa Medical Research, vol. 5, pp. 382–386 (1977).
Archives of Dermatology, vol. III, pp. 1293–1296 (Oct. 1975).
The Journal of Investigative Dermatology, vol. 64, pp. 268–272.
Canadian Veterinary Journal, vol. 20, pp. 45–48 (Feb. 1979).
Archives of Dermatology, vol. 113, pp. 1539–1542 (Nov. 1977).

Primary Examiner—John W. Rollins
Attorney, Agent, or Firm—Poms, Smith, Lande & Rose

[57] ABSTRACT

A dual phase solvent carrier system for topically applying at least one pharmaceutically active compound comprised of the active compound dissolved in at least one delivery solvent and at least one fugitive solvent, with a particularly useful composition for topically treating dermatophytic infections comprised of of griseofulvin, benzyl alcohol and at least one fugitive solvent.

21 Claims, 1 Drawing Sheet

DUAL PHASE SOLVENT CARRIER SYSTEM

BACKGROUND OF THE INVENTION

The present invention is directed to a dual phase carrier system for pharmaceutically active compounds and also to compssitions useful for the treatment of dermatomycoses fungal infections. In a specific embodiment, the invention is directed to a composition containing griseofulvin which is topically applied to dermatophytic infections.

In many applications, it is desirable to topically apply pharmaceutically active compounds. One particular application is the treatment of dermatophytic infections. A dermatophytic infection is caused by the invasion of fungi into the keratinized layers of the epidermis, hair and nails of human beings and other animals. There are numerous fungi, such as *T. rubrum, Microsporum Canis, T. interdigitale*, and other known fungi that can cause these types of infections. The treatment of these infections typically involves administering one or more known types of antifungal agents, e.g. griseofulvin, clotrimazole, miconazole nitrate and thiapendazole, either orally or topically depending on the particular anti-fungal agent used. While certain antifungal agents may be applied topically or orally, certain antifungal agents, e.g. griseofulvin, have generally only been administered orally. Typically, griseofulvin may be administered when the dermatophytic infection has not been successfully treated with the topical application of other antifungal agents.

Despite the effectiveness of orally administered griseofulvin there is concern that the oral use of griseofulvin includes a risk of toxicity and carcinogenesis. It is generally believed that these risks may be reduced if griseofulvin could be successfully topically administered. The topical administration of griseofulvin has been hindered by the lack of a suitable carrier, since griseofulvin can not be topically applied and absorbed through the dermis in its natural solid or powder state. Furthermore, griseofulvin is insoluble in water and only slightly soluble in common solvents, such as dimethylsulfoxide, dimethylformamide and acetone which are typically used as pharmaceutical carriers. The following articles generally discuss the topical application of griseofulvin using various carrier systems.

"Topical griseofulvin therapy of that which is called tinea pedis", by Goldman et al, *ASMC DermatoVenereologica*, line 39, page 454–460 (1959);

"The activity of various topical griseofulvin preparations and the appearance of oral griseofulvin in the stratum corneum", by Knight, *British Journal of Dermatology*, Vol. 91, pages 49–55 (1974);

"Topically applied griseofulvin in the treatment of superficial dermatomycoses in Egypt", by H. Abgel-Aal et al, *Journal International Medical Research*, Vol. 5, pages 382–286 (1977);

"Topically applied griseofulvin in prevention and treatment of Trichophyton mentagrophytes" by Epstein et al, *Archives of Dermatology*, Vol. 111, pages 1293–1296 (October 1975);

"Evaluation of the effectiveness of griseofulvin, tolnaftate, and placebo in the topical therapy of superficial dermatophytoses" by Zarowny et al, *The Journal of Investigative Dermatology*, Vol. 64 pages 268–272 (1975);

"Topical treatment of experimental ringworm in guinea pigs with griseiofulvin in dimethylfoxide" by Post and Saunders, *Canadian Veterinary Journal*, Vol. 20, pages 45–48 (February 1979);

"Topically applied antifungal agents" by Wallace et al, *Archives of Dermatology*, Vol. 113, pages 1539–1542 (November 1977).

The carrier systems discussed by these articles may be generally classified as consisting of highly volatile solvents, oily solvents or ointments. Some of these carrier systems were found to be ineffective, or if at least partially effective, exhibited other drawbacks. Generally, the highly volatile solvents, e.g. alcohol, dissipated before sufficient time had elapsed for the griseofulvin to be absorbed through the dermis, leaving a residue of griseofulvin powder on the dermis surface. The oily solvents or ointment carriers, even when demonstrated as a potentially effective as a carrier, typically was applied in relatively excessive amounts leaving an oily residue on the dermis even after the lapse of an extended period of time. Furthermore, some of the carrier solvents found effective, i.e. trichloroethanol and dimethylsulfoxide, caused irritation to the dermis when used over extended periods of time.

Topical griseofulvin compositions are also disclosed in U.S. Pat. No. 3,899,578, issued to Bird et al, Aug. 12, 1975. The disclosed compositions are comprised of griseofulvin dissolved in various high boiling, volatile solvents, e.g. propylene carbonate, dimethylphthalate, 3-phenoxypropanol, 4-chlorophenoxyethanol, phenoxyethanol, phenylethanol, eugenol and benzyl alcohol. Benzyl alcohol in combination with dimethyl phthalate, propylene carbonate or eugenol are disclosed as preferred solvent carriers. The useful compositon may be diluted with ethanol, n-propanol, isopropanol, propylene glycol or glycerol. However, the disclosed compositions would be generally classified as a gel, ointment or paste due to the large amount of the low volatile solvent used in their preparation. Thus, these compositions will leave an oily residue for a considerable amount of time after application. This potentially delays or hinders the absorption of griseofulvin since it is believed that griseofulvin preferably remain solubilized in the oily layer of the composition.

There thus remains a need for a topically applied solvent carrier system which does not cause irritation or leave an substantially large oily residue, which potentially delays or hinders absorption of the pharmaceutically active compound being applied, and particularly a carrier system for the topical application of griseofulvin.

SUMMARY OF THE INVENTION

The invention is directed to a unique solvent carrier system for the topical application of pharmaceutically active compounds, e.g. antifungal agents. This solvent carrier system comprises a first solvent phase of a relatively high boiling solvent and a second solvent phase of a relatively low boiling solvent and a pharmaceutically effective amount of a pharmaceutically active compound. Both solvents are compatible and co-soluble in each other and of the type into which the particular pharmaceutically active compound can be dissolved. When topically applied, the low boiling solvent will quickly dissipate due to the patient's body temperature, leaving a concentrated solution of the pharmaceutically active compound in the remaining high boiling solvent. Due to the low concentration of the high boiling solvent in the initial composition, the remaining layer is sufficiently thin enough to promote the absorption of the pharmaceutically active compound through the patient's dermis without the above discussed disadvantages.

In a specific embodiment, the invention is directed to a composition which is comprised of at least about 0.05 weight percent griseofulvin, from about 5 to about 15 weight percent benzyl alcohol, and a major amount of one or more pharmaceutically suitable low boiling organic solvents. This composition can be topically applied to dermatophytic infection for treating the same.

The invention is further directed to methods of making and using the composition.

BRIEF DESCRIPTION OF THE DRAWINGS

The present invention may be better understood and its numerous advantages and objectives will become apparent to those of ordinary skill in the art by reference to the accompanying drawings, wherein like reference numerals refer to like elements in the several figures, in which.

DESCRIPTION OF THE PREFERRED EMBODIMENTS

Figure 1:
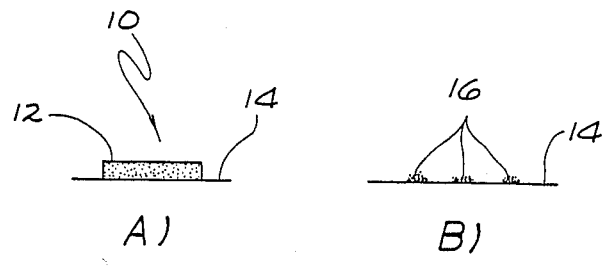
FIGS. 1A and 1B are schematic illustrations of one type of prior art solvent carrier system.

In accordance with one embodiment the invention is directed to a dual phase solvent carrier system for topically applying pharmaceutically active compounds. Specifically, the invention is directed to a solvent carrier system comprised of a pharmaceutically effective amount of a pharmaceutically active compound dissolved in a solution of one or more pharmaceutically acceptable delivery solvents, which for the purposes of the invention are those solvents which possess a relatively high boiling point, typically greater than 120° C., preferably in excess of 200° C., and one or more pharmaceutically acceptable fugitive solvents, which for the purposes of the invention are those solvents which possess a relatively low boiling point, typically less than about 110° C., preferably less than about 85° C.

An advantage of using the dual phase solvent carrier system of the invention is that a pharmaceutically effective amount of a pharmaceutically active compound can be delivered to the site of infection which is to be treated without an excessive amount of an oily residue remaining after a period of time. "Pharmaceutically effective amount" shall mean the amount of the compound dissolved into the dual phase solvent carrier system that is effective for achieving the desired results, i.e. treatment, cure or control of a specific infection or disease. This amount will vary depending upon the particular active compound and the disease or infection being treated.

The dual phase solvent carrier system of the invention will generally be comprised of from about 5 to about 15 weight percent of the delivery solvent and of a major amount, typically more than fifty percent of the fugitive solvent. Preferably, the fugitive solvent will comprise from about 95 to about 75 weight percent of the carrier system.

The carrier system of the invention may be used to topically apply any suitable pharmaceutically active compound, primarily hydrophobic compounds. Preferably the active compound is an antifungal agent, e.g. miconazole nitrate, thiapendazole, tolnaftate, clotrimazole or griseofulvin, and most preferably griseofulvin. The active compound will be present in the carrier system at a pharmaceutically effective amount for the particular compound and the disease being treated. Preferably, the active compound will comprise from about 0.05 to about 3 weight percent of the carrier system.

An advantage of using the dual phase carrier system of the invention is that following topical application, a very thin layer of the delivery solvent will remain upon the affected area as the fugitive solvent quickly dissipates. The delivery solvent, which remains on the affected area, possesses a greater concentration of the pharmaceutically active compound than the starting carrier system. A concentration of the active compound on the patient's dermis of 5–20 or more fold can be achieved by using this system. Furthermore, as stated, the amount of the system remaining on the affected area after application is significantly reduced. Even at the higher concentrations of the delivery solvent the amount of the carrier system remaining will be less than about 15 percent of the initial amount of carrier system. This not only concentrates the active compound, but it is believed facilitates the transport of the active compound through the patient's dermis. It is believed that the remaining thin layer of the delivery solvent provides a sufficiently greater surface area to volume ratio which promotes the dissipation of the delivery solvent slowly. It is further believed that this slow dissipation induces the transport of the active compound through the dermis. When large amounts of a low volatile solvent remain on the dermis it has been found that the active compound will preferentially remain in the solvent and be absorbed slowly if at all through the dermis. This is the situation with previously used ointment or gel type carrier systems. Thus not only does the carrier system of the invention provide a means for applying a concentrated amount of an active compound but also promotes transport of the compound through the dermis. It should be noted that the above discussion concerning the mechanism of absorption is merely a theory and should not be taken in any manner to limit the scope of the invention.

The carrier system may be prepared by admixing the solvents and active compound in a suitable manner which assures the solubilization of the compound in the solvents. Furthermore, the carrier system may be applied to the affected area by any suitable means.

Referring to FIGS. 1A and B, a schematic illustration of a prior art solvent delivery system of the type which comprises a relatively low boiling organic solvent, e.g. an alcohol, is seen generally at 10. As shown in FIG. 1A, a solution 12 of a pharmaceutically active compound (illustrated as a powder) in the low boiling solvent is applied to a patient's dermis 14. The solvent, which is volatile, quickly dissipates due to the temperature of the patient's dermis, typically about 32° C., leaving as a residue the solid or powder form of the active compound, as seen generally at 16. The active compound powder residue 16 will not be absorbed through the dermis 14. Furthermore, little, if any, of the active compound will be absorbed through the patient's dermis 14 prior to dissipation or evaporation of the solvent. Thus this type of prior art carrier system is generally ineffective as a delivery system for most pharmaceutically active compounds.

Figure 2:
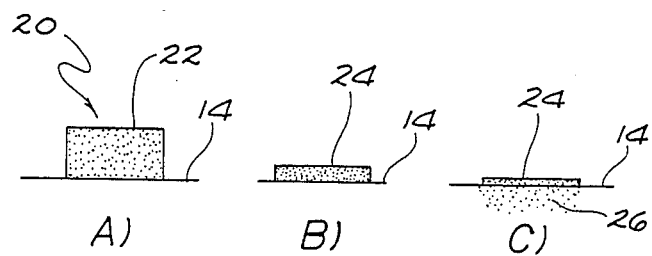
FIGS. 2A, B and C are schematic illustrations of a dual-phase carrier system in accordance with an embodiment of the invention.

Referring now to FIGS. 2A, B and C, a schematic illustration of the dual phase solvent carrier system of the invention applied to the patient's dermis 14 is seen generally at 20. As stated above, the system 20 is comprised of a solution 22 of from about 5 to about 15 weight percent of one or more delivery solvents (high boiling point solvents) and a major amount of one or more fugitive solvents (low boiling point solvents) into which a pharmaceutically active compound is dissolved. Upon topical administration of the solution 22 to the patient's dermis 14, the fugitive solvent will be substantially dissipated or evaporated due to the dermis 14 temperature (about 32° C.). As seen in FIG. 2B, this leaves a residue solution 24 of the pharmaceutically active compound concentrated in the delivery solvent. A comparison of FIGS. 2B and 2C schematically illustrates that as the delivery solvent or residue solution 24 slowly dissipates over a sufficient enough period of time the active compound is absorbed through the dermis 14, represented generally at 26 as a powder. This allows the active compound to be delivered to and act upon the specific disease or infection.

It should be noted that the solvents utilized should be compatible and of the types into which the active compound may be dissolved. Furthermore, the delivery solvent should have a sufficiently high enough boiling point to ensure a residue time for the solution 24 upon the dermis 14 sufficient enough to promote the absorption of the active compound. Examples of suitable delivery solvents include, but are not limited to, propylene carbonate, dimethylphthalate, 3-phenoxypropanol, 4-chlorophenoxyethanol, phenoxyethanol, phenylethanol, eugenol, benzyl alcohol and chloroform. Suitable fugitative solvents include, but are not limited to, ethanol, n-propanol, isopropanol, propylene glycol, butyl alcohol and acetone.

In accordance with another embodiment the invention is directed to a particularly useful carrier system for treating dermatophytic infections. This carrier system is a composition comprised of benzyl alcohol, as the delivery solvent, one or more fugitive solvents (as defined above) and a pharmaceutically effective amount of griseofulvin. This embodiment of the invention has been found unexpectedly superior for topically delivering pharmaceutically effective amounts of the griseofulvin to treat dermatophytic infections.

There are various types of dermatophytic infections which this composition of the invention may be used to treat. Generally, this composition may be used to treat the various dermatophytic infections, e.g. tinea pedis, tinea capitis and tinea corporis. These types of infections may be caused by numerous fungi, e.g. those classified under the genera: trichophyton, microsporum or epidermophyton.

The antifungal agent griseofulvin used to treat these fungal infections in accordance with this embodiment of the invention is represented by the following general formula:

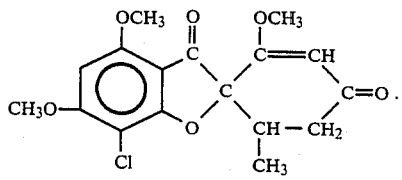

The composition is comprised of at least about 0.05 weight percent griseofulvin, preferably from about 0.5 to about 3 weight percent and more preferably about 1 weight percent.

The delivery solvent used in this composition is as stated advantageously benzyl alcohol. It has been found that benzyl alcohol is particularly well suited to act as the delivery solvent for the griseofulvin. Generally, the composition will be comprised of from about 5 weight percent to about 15 weight percent benzyl alcohol, more preferably about 10 weight percent. It has been unexpectedly found that griseofulvin is soluble in benzyl alcohol at high concentrations, i.e. 8 to 20 weight percent concentration, at room temperature and even more importantly at elevated temperatures, such as about 32° C. which is the temperature of the patient's skin to which the composition will be applied. This assures that the griseofulvin will be soluble in the layer of benzyl alcohol remaining after the dissipation of the fugitive solvent. Furthermore, it has unexpectedly been found that the griseofulvin remains solubilized in benzyl alcohol as the fugitive solvent dissipates, and that the benzyl alcohol solution remains on the dermis, even as a thin layer, for a sufficient enough period of time allowing the griseofulvin to be absorbed into the dermis.

The fugitive solvent will comprise a major amount of the composition, preferably from about 95 to about 75 weight percent, more preferably about 90 weight percent of the composition. More, than one fugitive solvent may be utilized in preparing the compositon with the proviso that the boiling point of the fugitive solvents not be effected to make them less volatile. Suitable fugitive solvents include, but are not limited to, isopropyl alcohol, acetone, n-propanol, propylene glycol, ethanol and butyl alcohol. It should be noted that the fugitive solvents which are useful for the practice of the invention are those compatible with the benzyl alcohol and those in which the griseofulvin is soluble.

Other compounds or additives may be present in the composition, e.g. other antifungal agents, solubilizing agents, keratolitic agents, aliphatic compounds with antifungal activity and solvent capacity (i.e. undecylenic acid). Preferably, the composition contains a pharmaceutically effective amount of a second antifungal agent, e.g. miconazole nitrate, thiapendazole, tolnaflate, or clotrimazole, preferably from about 0.05 to about 3 weight percent of a second antifungal agent, and more preferably clotrimazole as the second antifungal agent.

The composition of the invention may be prepared by any suitable technique, e.g. preparing or admixing the solvents and subsequently dissolving therein the griseofulvin and other additives. Preferably, the griseofulvin is first dissolved in the benzyl alcohol at an amount to provide the desired concentration of the griseofulvin in the final composition. The amount of benzyl alcohol into which the griseofulvin is dissolved shall also be sufficient to provide the desired concentration of benzyl alcohol in the final composition. This solution of griseofulvin in benzyl alcohol is then admixed with the desired fugitive solvent or solvents such as isopropyl alcohol, to provide the desired composition. Preferably, any other additives are dissolved along with the griseofulvin into the benzyl alcohol.

While the dissolving of the griseofulvin in benzyl alcohol may be carried out at room temperature, it is preferable that the benzyl alcohol be heated to a temperature of from about 400° C. to about 500° C. prior to dissolving the griseofulvin or other additives. This accelerates the solubilizing of the griseofulvin into the benzyl alcohol. The griseofulvin is preferably used in its microcrystalline form. The dissolving of the benzyl alcohol-griseofulvin solution into the fugitive solvent or solvents is typically carried out at room temperature.

The resulting composition is topically applied directly to the infected site. After application the fugitive solvent or solvents will quickly dissipate by evaporation, due to the body temperature of the patient, leaving as a residue a thin film of the benzyl alcohol-griseofulvin solution on the effected area. It has unexpectedly been found that even when the griseofulvin becomes highly concentrated in the benzyl alcohol, as the fugitive solvent dissipates, it remains in solution and does not precipitate out of the benzyl alcohol. This is critical since any griseofulvin which precipitates out of the benzyl alcohol would not be in a form to be absorbed into the dermis. Furthermore, the benzyl alcohol is stable enough at the given temperature of the patient's dermis to remain for a sufficient enough time to allow absorption into the dermis.

The composition may be applied to the infected area by any satisfactory means, such as by a cotton swab, an eye dropper or aerosol spray. The effective amount of the composition applied to the infected area is such to provide a thin layer of the benzyl alcohol-gfriseofulvin solution after dissipation or absorption of the fugitive solvent. The precise amount of the composition applied is not critical, however excessive application will not be beneficial.

The utilization of this composition ensures that the griseofulvin remains dissolved in a thin layer of solvent for a sufficient enough time on the patient's dermis to allow for absorption of the griseofulvin. Furthermore, the topical application of griseofulvin using this composition allows a reduction in the amount of griseofulvin given the patient in comparison with oral administration. This reduces the potential risks associated with the oral administration of griseofulvin as discussed above and the potential of skin irritation caused by the solvent.

EXAMPLE

A griseofulvin composition of the invention was prepared comprised of 1 weight percent griseofulvin, 10 weight percent benzyl alcohol, 40 weight percent acetone and 50 weight percent isopropyl alcohol. This composition was prepared by dissolving the griseofulvin into benzyl alcohol that was heated to about 40° C. This resulting composition was dissolved into the acetone and subsequently into the isopropyl alcohol. The final composition showed no indication of griseofulvin precipitation.

This composition was applied to a tinea pedis infection, using a cotton swab, every 7 to 10 days. The outbreak of the infection was successfully controlled by this application with no observed secondary skin irritations caused by the composition. Previously, a composition containing 1 weight percent griseofulvin, 1 weight percent chloroform with the remainder being isopropyl alcohol was topically applied to the same tinea pedis infection. This composition was only effective in controlling the infection by daily applications. Thus the administration of the griseofulvin composition of the invention was unexpectedly superior in controlling the outbreak of the tinea pedis infection than the previously used composition. This demonstrates that the griseofulvin composition of the invention provides a better solvent carrier system for the griseofulvin.

The composition described in the above example may also be used to control other dermatophytic infections, e.g. tinea capitis and tinea corporis.

While the preferred embodiments have been described, various modifications and substitutions may be made thereto without departing from the spirit and scope of this invention. Accordingly, it is to be understood that the present invention has been described by way of illustration and not limitation.

What is claimed is:

1. A dual phase solvent carrier system comprising:
   a pharmaceutically effective amount of a pharmaceutically active compound;
   from about 5 to about 15 weight percent of one or more delivery solvents; and
   a major amount of one or more fugitive solvents having a boiling point of less than 110° C.

2. The system of claim 1 wherein said fugitive solvent is present at from about 95 to about 75 weight percent of said system.

3. The system of claim 2 wherein said fugitive solvent has a boiling point of less than about 85° C.

4. The system of claim 3 wherein said pharmaceutically active compound is present at from about 0.05 to about 3 weight percent of the system.

5. The system of claim 4 wherein said pharmaceutically active compound is selected from the group consisting of micronazole nitrate, thiapendazole, tolnaftate, clotrimazole or griseofulvin.

6. The system of claim 4 wherein said pharmaceutically active compound is griseofulvin.

7. A composition comprising:
   at least about 0.05 weight percent griseofulvin;
   from about 5 to about 15 weight percent benzyl alcohol; and
   a major amount of one or more pharmaceutically acceptable fugitive solvents having a boiling point of less than 110° C.

8. The composition of claim 7 wherein said fugitive solvent comprises from about 75 to about 95 weight percent of said composition.

9. The compositon of claim 8 wherein said griseofulvin is present from about 0.5 to about 3 weight percent of said composition.

10. The composition of claim 8 wherein said griseofulvin is present in said composition at about 1 weight percent.

11. The composition of claim 9 wherein said benzyl alcohol is present in said composition at about 10 weight percent.

12. The composition of claim 11 further including a pharmaceutically effective amount of minconazole nitrate, thiapendazole, tolnaftate or clotrimazole.

13. The composition of claim 11 wherein said fugitive solvents have a boiling point of less than about 85° C.

14. The composition of claim 11 wherein said one or more fugitive solvents are selected from the group consisting of n-propanol, isopropyl alcohol, acetone, ethyl alcohol, propylene glycol and butyl alcohol.

15. The composition of claim 14 further including from about 0.05 to about 3 weight percent of miconazole nitrate, thiapendazole, tolnaftate or clotrimazole.

16. The compositin of claim 11 wherein said fugitive solvent comprises about 90 weight percent of said composition.

17. A method of treating a dermatophytic infection comprising topically applying an effective amount of the composition of claim 7 to said infection.

18. A method of treating a dermatophytic infection comprising topically applying an effective amount of the composition of claim 8 to said infection.

19. A method of treating a dermatophytic infection comprising topically applying an effective amount of the composition of claim 15 to said infection.

20. A method of treating a dermaphytic infection comprising applying to said infection an effective amount of a composition comprising from about 0.5 to about 3 weight percent griseofulvin; from about 5 to about 15 weight percent benzyl alcohol and from about 75 to about 95 weight percent one or more fugitive solvents.

21. The method of claim 20 wherein said composition further comprises a pharmaceutically effective amount of clotrimazole.

* * * * *